United States Patent
Drumm et al.

(10) Patent No.: US 10,987,343 B2
(45) Date of Patent: Apr. 27, 2021

(54) COMPOSITIONS AND METHODS FOR TREATING PULMONARY DISEASES

(71) Applicant: CASE WESTERN RESERVE UNIVERSITY, Cleveland, OH (US)

(72) Inventors: Mitchell L. Drumm, Cleveland, OH (US); Rebecca J. Darrah, Cleveland, OH (US); Frank J. Jacono, Cleveland, OH (US); Anna L. Mitchell, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/767,114

(22) PCT Filed: Oct. 11, 2016

(86) PCT No.: PCT/US2016/056440
§ 371 (c)(1),
(2) Date: Apr. 9, 2018

(87) PCT Pub. No.: WO2017/062988
PCT Pub. Date: Apr. 13, 2017

(65) Prior Publication Data
US 2019/0070153 A1    Mar. 7, 2019

Related U.S. Application Data

(60) Provisional application No. 62/239,520, filed on Oct. 9, 2015.

(51) Int. Cl.
| | |
|---|---|
| *A61K 31/437* | (2006.01) |
| *A61K 31/47* | (2006.01) |
| *A61P 11/12* | (2006.01) |
| *A61P 11/06* | (2006.01) |
| *A61P 11/08* | (2006.01) |

(52) U.S. Cl.
CPC .......... *A61K 31/437* (2013.01); *A61K 31/47* (2013.01); *A61P 11/06* (2018.01); *A61P 11/08* (2018.01); *A61P 11/12* (2018.01)

(58) Field of Classification Search
CPC ........ A51K 31/47; A61K 31/437; A61P 11/12
See application file for complete search history.

(56) References Cited

U.S. PATENT DOCUMENTS

| | | |
|---|---|---|
| 2010/0221340 A1 | 9/2010 | Yan et al. |
| 2010/0316628 A1 | 12/2010 | Breton et al. |
| 2011/0092463 A1 | 4/2011 | Raud et al. |
| 2014/0315808 A1 | 10/2014 | Weinstein et al. |

OTHER PUBLICATIONS

Jerng et al. 'Role of the renin-angiotensin system in ventilator-induced lung injury: an in vivo study in a rat model', Thorax 2007, vol. 62, pp. 527-535.

*Primary Examiner* — Samira J Jean-Louis
(74) *Attorney, Agent, or Firm* — Tarolli, Sundheim, Covell & Tummino LLP

(57) ABSTRACT

A method of treating a pulmonary disease in a subject in need thereof includes administering to the subject a therapeutically effective amount of an agent that inhibits the renin-angiotensin signaling pathway.

10 Claims, 2 Drawing Sheets

COMPOSITIONS AND METHODS FOR TREATING PULMONARY DISEASES

RELATED APPLICATION

This application claims priority from U.S. Provisional Application No. 62/239,520, filed Oct. 9, 2015, the subject matter of which is incorporated herein by reference in its entirety.

BACKGROUND

Progressive, debilitating pulmonary disease remains the primary cause of morbidity and mortality for individuals with cystic fibrosis (CF). CF is caused by mutations in the cystic fibrosis transmembrane conductance regulator gene (CFTR), and affects 1/3000 individuals in the United States. The discovery of CFTR-corrector therapies has led to recent advances in CF treatment options. These therapies have restored partial function of CFTR for individuals with specific mutations, resulting in successful attenuation of some CF symptoms in approximately 4% of the CF patient population. However, these new corrector drugs are by no means curative, only modestly improving pulmonary function, and do not appear to improve other important components of the pulmonary disease. Thus, there remains a strong clinical need for improved CF therapies that can not only augment the corrector therapies, but also benefit patients regardless of CFTR genotype.

SUMMARY

Embodiments described herein relate to methods of treating pulmonary diseases, such as cystic fibrosis (CF), asthma, and chronic obstructive pulmonary disease (COPD), in subjects as well as to methods of treating or slowing the progression of lung disease in a subject having or at risk of cystic fibrosis (CF), asthma, or chronic obstructive pulmonary disease (COPD), by administering to the subject an agent that inhibits the renin-angiotensin signaling pathway.

In some embodiments, the agent that inhibits the renin-angiotensin signaling pathway can be an AGTR2 antagonist. Examples of AGTR2 antagonists include 4,5,6,7-tetrahydro-1H-imidazo[4,5-c]pyridine-6-carboxylic acid analogs. In some embodiments, the agent can include 1-(4-Dimethylamino-3-methylphenyl)methyl-5-diphenylacetyl-4,5,6,7-tetrahy-dro-1H-imidazo[4,5-c]-pyridine-6-carboxylic acid (PD-123,319); 1-(3-methyl-4-methoxyphenyl)-methyl-5-diphenylacetyl-4,5,6,7-tetrahydro-1-H-imidazo[4,5-c]pyridine-6-carboxylic acid (PD-121,981); and 1-(((4-amino-3-methylphenyl)methyl)-5-(diphenylacetyl)-4,5,6,7-tetrahydro-1H-imidazo(4,5c)pyridine-6-carboxylic acid (PD-123,177), (S)-2-(Diphenylacetyl)-1,2,3,4-tetrahydro-6-methoxy-5-(phenylmethoxy)-3-isoquinolinecarboxylic acid, their prodrugs, and pharmaceutically acceptable salts thereof.

In other embodiments, the AGTR2 antagonist is selected from antigen-binding molecules that are immuno-interactive with an AGTR2 polypeptide.

In still other embodiments, the AGTR2 antagonist is selected from nucleic acid molecules that inhibit or otherwise reduce the level or functional activity of an expression product of an AGTR2 gene, illustrative examples of which include antisense molecules, ribozymes and RNAi molecules.

In some embodiments, the AGTR2 antagonist is administered at amount effective to provide improvements to pulmonary function and/or lung mechanics and/or airway resistance. The improvements to pulmonary function and/or lung mechanics and/or airway resistance can include, for example, at least one of increased respiratory compliance, decreased elastance of the respiratory system, decreased respiratory tissue damping and elastance, or increased static respiratory tissue compliance.

In still other embodiments, the AGTR2 antagonist can be administered to the subject in combination with at least one of an ACE inhibitor, a renin inhibitor, or an AGTR1 agonist.

DETAILED DESCRIPTION

Figure 1:
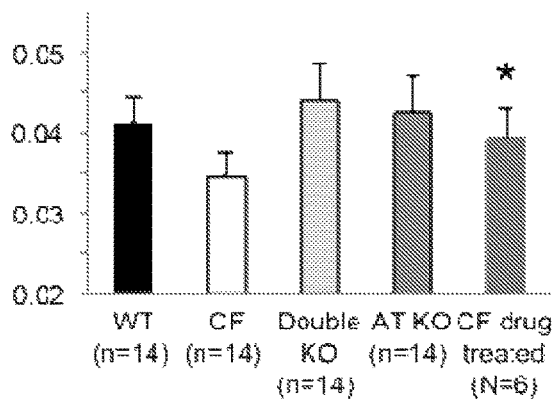
FIGS. 1(A-E) illustrate graphs showing forced mechanical ventilation (FlexiVent) data demonstrating that CF mice (white bars) have significantly decreased compliance, and increased elastance of the respiratory system; increased tissue damping and elastance, decreased static tissue compliance, and an altered inhalation/exhalation shape (K) (compared to WT mice; black bars). Knocking out the Agtr2 gene in the CF mice (Double KO, light grey bars) restores the pulmonary mechanics (except shape parameter) to WT levels, and treatment of CF mice with an AGTR2 inhibitor (dark bars) also results in improved pulmonary mechanics (except shape parameter). AGTR2 knockout mice (AT KO; dark grey bars) are indistinguishable from WT mice.
Figure 1:
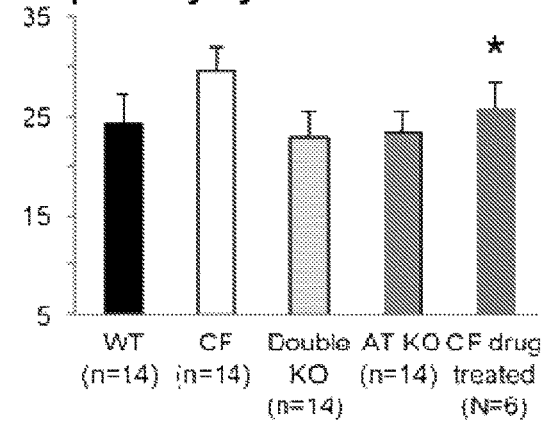
Figure 1:
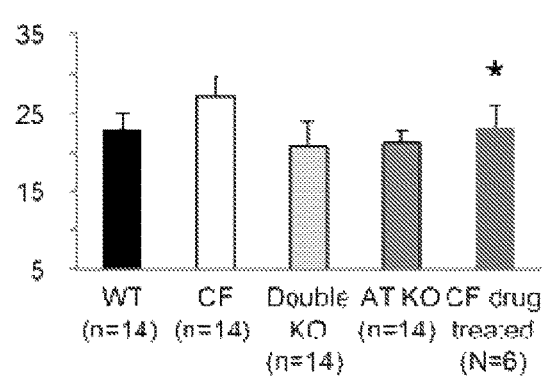
Figure 1:
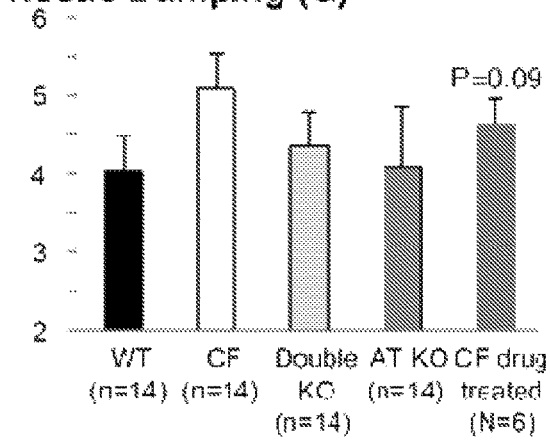
Figure 1:
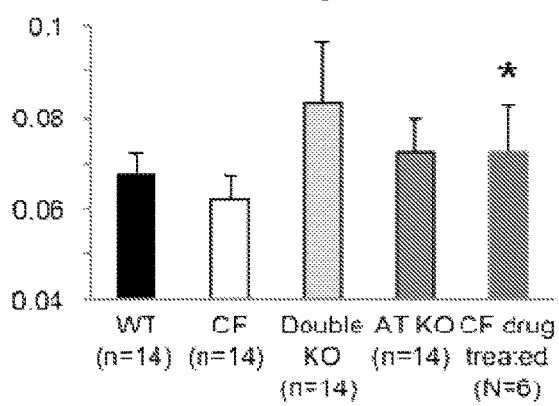
Figure 1:
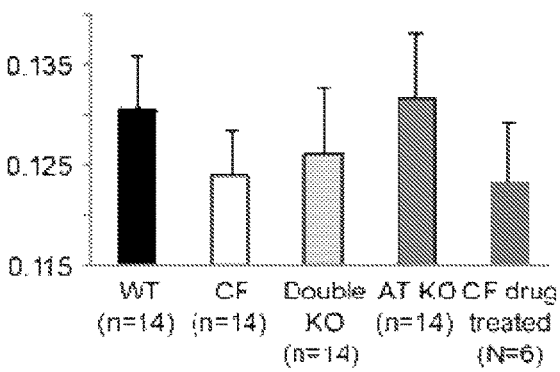

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The term "about" refers to a quantity, level, value, dimension, size, or amount that varies by as much as 30%, 25%, 20%, 15% or 10% to a reference quantity, level, value, dimension, size, or amount.

The term "acyl" denotes a group containing the moiety C=O (and not being a carboxylic acid, ester or amide) Preferred acyl includes C(O)—R, wherein R is hydrogen or an alkyl, alkenyl, alkynyl, aryl, heteroaryl or heterocyclyl residue, preferably a $C_{1-20}$ residue.

If a number of carbon atoms is not specified, the term "alkenyl," unless otherwise indicated, refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$alkenyl" means an alkenyl radical having from 2 to 6 carbon atoms. Alkenyl groups include, but are not limited to, ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkenylene" refers to a straight, branched or cyclic, preferably straight or branched, bivalent aliphatic hydrocarbon group, preferably having from 2 to about 20 carbon atoms and at least one double bond, more preferably 2 to 12 carbons, even more preferably lower alkenylene. The alkenylene group is optionally substituted with one or more "alkyl group substituents." There may be optionally inserted along the alkenylene group one or more oxygen, sulfur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

The terms "alkoxy," "alkenoxy," "alkynoxy," "aryloxy," "heteroaryloxy," "heterocyclyloxy" and "acyloxy" respectively denote alkyl, alkenyl, alkynyl aryl, heteroaryl, heterocyclyl and acyl groups as herein defined when linked by oxygen.

"Alkoxy," unless otherwise indicated, represents either a cyclic or non-cyclic alkyl group attached through an oxygen bridge. "Alkoxy" therefore encompasses the definitions of alkyl and cycloalkyl below. For example, alkoxy groups include but are not limited to methoxy, oxy ethoxy, n-propyloxy, i-propyloxy, cyclopentyloxy and cyclohexyloxy.

The term, "alkyl" is intended to include both branched and straight-chain saturated aliphatic hydrocarbon group and may have a specified number of carbon atoms. For example, $C_1$-$C_{10}$, as in "$C_1$-$C_{10}$alkyl" is defined to include groups having 1, 2, 3, 4, 5, 6, 7, 8, 9 or 10 carbons in linear or branched arrangement. For example, "$C_1$-$C_{10}$alkyl" specifically includes, but is not limited to, methyl, ethyl, n-propyl, i-propyl, n-butyl, t-butyl, i-butyl, pentyl, hexyl, heptyl, octyl, nonyl, decyl.

The term, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulfur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkylidene" refers to a bivalent group, such as =CR9R0, which is attached to one atom of another group, forming a double bond. Exemplary alkylidene groups are methylidene (=CH$_2$) and ethylidene (=CHCH$_3$). As used herein, "arylalkylidene" refers to an alkylidene group in which either R9 or R0 is an aryl group. As used herein, "diarylalkylidene" refers to an alkylidene group in which R9 and R0 are both aryl groups. "Diheteroarylalkylidene" refers to an alkylidene group in which R9 and R0 are both heteroaryl groups.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$alkynyl" means an alkynyl radical having from 2 to 6 carbon atoms. Alkynyl groups include, but are not limited to, ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as, for example, —CH$_2$Ph, —CH$_2$CH$_2$Ph, CH(CH$_3$)CH$_2$CH(CH$_3$)Ph.

The term "alkynylene" refers to a straight, branched or cyclic, preferably straight or branched, bivalent aliphatic hydrocarbon group, preferably having from 2 to about 20 carbon atoms and at least one triple bond, more preferably 2 to 12 carbons, even more preferably lower alkynylene. The alkynylene group is optionally substituted with one or more "alkyl group substituents." There may be optionally inserted along the alkynylene group one or more oxygen, sulfur or substituted or unsubstituted nitrogen atoms, where the nitrogen substituent is alkyl as previously described. The term "lower alkynylene" refers to alkynylene groups having 2 to 6 carbons. Preferred alkynylene groups are lower alkynylene, with alkynylene of 3 to 4 carbon atoms being particularly preferred.

The term "AGTR2 antagonist" means an agent that decreases or inhibits the biological activity of an AGTR2 gene or an expression product thereof including an AGTR2 polypeptide.

The term "asthma" referrers to a chronic lung disease characterized by inflammation and constriction of the airways. Asthma causes recurring periods of wheezing, tightness of the chest, shortness of breath, and coughing. Swelling and overproduction of mucus can cause further airway constriction and worsening of symptoms. There is evidence that increased matrix degradation may occur in asthma, and this may contribute to mechanical changes in the airways in asthma.

The term "AGTR2" polypeptide means an angiotensin II type 2 receptor polypeptide that can bind angiotensin II and/or one or more other ligands. The term "AGTR2" encompasses vertebrate homologs of AGTR2 family members, including, but not limited to, mammalian, reptilian and avian homologs. Representative mammalian homologs of AGTR2 family members include, but are not limited to, murine and human homologs.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

As used herein, "aromatic" or "aryl" is intended to mean, unless otherwise indicated, any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

"Aralkyl" means alkyl as defined above which is substituted with an aryl group as defined above, e.g., —CH$_2$phenyl, —(CH$_2$)$_2$phenyl, —(CH$_2$)$_3$phenyl, —H$_2$CH(CH$_3$)CH$_2$phenyl, and the like and derivatives thereof.

The term "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulfur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

The "arylidene" refers to an unsaturated cyclic bivalent group where both points of attachment are on the same atom of the ring. Exemplary arylidene groups include, but are not limited to, quinone methide moieties that have the formula:

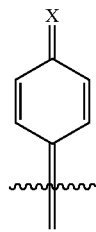

where X is O, S or NR9. "Heteroarylidene" groups are arylidene groups where one or two, preferably two, of the atoms in the ring are heteroatoms, such as, but not limited to, O, S and N.

The term "biological activity" means any observable effect flowing from the interaction between an AGTR2 polypeptide and a ligand. Representative, but non-limiting, examples of biological activity in the context of the present invention include association of an AGTR2 with a ligand, including an endogenous ligand such as angiotensin II or an AGTR2 antagonist. The term "biological activity" also encompasses both the inhibition and the induction of the expression of an AGTR2 polypeptide. Further, the term "biological activity" encompasses any and all effects flowing from the binding of a ligand by an AGTR2 polypeptide.

The term "Chronic Obstructive Pulmonary Disease" (COPD) is a common lung disease that is often associated with chronic bronchitis or emphysema. Symptoms can often include cough, mucus build up, fatigue, wheezing, and respiratory infection.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "cycloalkenyl" means a monocyclic unsaturated hydrocarbon group and may have a specified number of carbon atoms. For example, "cycloalkenyl" includes but is not limited to, cyclobutenyl, cyclopentenyl, methylcyclopentenyl, cyclohexenyl and cyclohexadienyl.

The term "cycloalkyl" or "aliphatic ring" means a monocyclic saturated aliphatic hydrocarbon group and may have a specified number of carbon atoms. For example, "cycloalkyl" includes, but is not limited to, cyclopropyl, methylcyclopropyl, 2,2-dimethyl-cyclobutyl, 2-ethyl-cyclopentyl, cyclohexyl.

The term cystic fibrosis refers to a recessive multi-system genetic disease characterized by abnormal transport of chloride and sodium across epithelium, leading to thick, viscous secretions in the lungs, pancreas, liver, intestine and reproductive tract. Cystic fibrosis is caused by a mutation in the gene for the protein cystic fibrosis transmembrane conductance regulator (CFTR). Lung disease results from clogging of the airways due to mucus build-up, decreased mucociliary clearance, and resulting inflammation, which can cause fibrotic injury and structural changes to the lungs. The fibrotic lung damage progresses over time leading some cystic fibrosis patients to require lung transplant.

By "effective amount", in the context of treating or preventing a condition is meant the administration of that amount of active to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The terms "halo" or "halogen" are intended to include chloro, fluoro, bromo and iodo.

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

The term "heteroaryl" or "heteroaromatic," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

The term "heteroarylene," refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —$CH_2$pyrrolidin-1-yl, —$(CH_2)_2$piperidin-1-yl, and the like, and derivatives thereof.

The term "hydrocarbyl" as used herein includes any radical containing carbon and hydrogen including saturated, unsaturated, aromatic, straight or branched chain or cyclic including polycyclic groups. Hydrocarbyl includes but is not limited to $C_1$-$C_8$alkyl, $C_2$-$C_8$alkenyl, $C_2$-$C_8$alkynyl, $C_3$-$C_{10}$cycloalkyl, aryl such as phenyl and naphthyl, Ar($C_1$-$C_8$)alkyl such as benzyl, any of which may be optionally substituted.

By "pharmaceutically acceptable carrier" is meant a solid or liquid filler, diluent or encapsulating substance that may be safely used in topical, local or systemic administration.

The terms "pharmaceutically compatible salt" and "pharmaceutically acceptable salt" are used interchangeably herein to refer to a salt which is toxicologically safe for human and animal administration. This salt may be selected from a group including hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. Pharmaceutically acceptable salts include both the metallic (inorganic) salts and organic salts; a non-exhaustive list of which is given in Remington's Pharmaceutical Sciences 17th Edition, pg. 1418 (1985). It is well known to one skilled in the art that an appropriate salt form is chosen based on physical and chemical stability, flowability, hydroscopicity and solubility.

"Phenylalkyl" means alkyl as defined above which is substituted with phenyl, e.g., —$CH_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

The term "prodrug" is used in its broadest sense and encompasses those compounds that are converted in vivo to an AGTR2 antagonist according to the invention. Such compounds would readily occur to those of skill in the art, and include, for example, compounds where a free hydroxy group is converted into an ester derivative.

As used herein, "pseudohalides" are groups that behave substantially similar to halides. Such groups can be used in the same manner and treated in the same manner as halides (X, in which X is a halogen, such as Cl or Br). Pseudohalides include, but are not limited to cyanide, cyanate, thiocyanate, selenocyanate, trifluoromethyl and azide.

The terms "subject" or "individual" or "patient", used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment or prophylaxis of inflammatory pain. However, it will be understood that the aforementioned terms do not imply that symptoms are present.

"Stereoisomers" refer to any two or more isomers that have the same molecular constitution and differ only in the three dimensional arrangement of their atomic groupings in space. Stereoisomers may be diastereoisomers or enantiomers. It will be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

The term "substituted" and variants such as "optionally substituted" as used herein, unless otherwise indicated, mean that a substituent may be further substituted by one or more additional substituents, which may be optional or otherwise.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants.

Embodiments described herein relate to methods of treating pulmonary diseases, such as cystic fibrosis (CF), asthma, and chronic obstructive pulmonary disease (COPD), in a subject as well as to methods of treating or slowing the progression of lung disease in a subject having or at risk of CF, asthma, or COPD, by administering to the subject an agent that inhibits the renin-angiotensin signaling pathway. As shown in the Examples, it was found that CF mice genetically modified with a deletion of the AGTR2 gene had a reversal and normalization of pulmonary function. Treatment of CF mice with an AGTR2 antagonist also successfully restored pulmonary function and enhanced the survival rate of the mice compared to controls. These findings identify a role for renin-angiotensin signaling in pulmonary diseases, such as CF, asthma, and COPD, and more specifically show that inhibition or reduction of AGTR2 signaling in the respiratory system of subjects with pulmonary disease, can be used to restore pulmonary function and enhance survival of subjects with chronic lung diseases.

In some embodiments, the method described herein can include administering to a subject with a chronic pulmonary disease, such as CF, asthma, and COPD, a therapeutically effective amount of an AGTR2 antagonist such that at least one feature of symptom of the pulmonary disease is reduced in intensity, frequency, or severity or has delayed onset. In some embodiments, a subject with a chronic pulmonary disease treated with an AGTR2 antagonist can have an improvement or at least partial restoration in pulmonary mechanics, including at least one of respiratory system compliance, respiratory system elastance, respiratory tissue elastance, respiratory tissue damping, and respiratory static tissue compliance.

The chronic pulmonary diseases to be treated can include, for example, cystic fibrosis, asthma, and chronic obstructive pulmonary disease. Treating chronic pulmonary diseases, such as cystic fibrosis (CF), may mean accomplishing one or more of the following: reducing the severity of one or more pulmonary disease symptoms; limiting or preventing development of one or more pulmonary disease symptoms; inhibiting worsening of one or more pulmonary disease symptoms; and limiting or preventing recurrence of one or more pulmonary disease symptoms in subjects that were previously symptomatic for the relevant pulmonary disease symptom.

Common symptoms of subjects suffering from chronic pulmonary diseases, such as cystic fibrosis, include, but are not limited to, accumulation of thick mucus, copious phlegm production, frequent chest infections, frequent coughing, frequent shortness of breath, inflammation, decreased ability to exercise, opportunistic infections of the lung and sinus (including but not limited to *Staphylococcus aureus, Haemophilus influenzae, Mycobacterium avium*, and *Pseudomonas aeruginosa*), pneumonia, tuberculosis, bronchiectasis, hemoptysis, pulmonary hypertension (and resulting heart failure), hypoxia, respiratory failure, allergic bronchopulmonary aspergillosis, mucus in the paranasal sinuses, sinus infection, facial pain, fever, excessive nasal drainage, development of nasal polyps, cardiorespiratory complications, CF-related diabetes, rectal prolapse, pancreatitis, malabsorption, intestinal blockage, exocrine pancreatic insufficiency, bile duct blockage, and liver cirrhosis.

In some embodiments, the symptoms of chronic pulmonary diseases, such as cystic fibrosis, comprise decreased respiratory compliance, increased elastance of the respiratory system, increased respiratory tissue damping and elastance, and decreased static respiratory tissue compliance and treatment of a subject having cystic fibrosis with an AGTR2 antagonist can result in restoration of pulmonary mechanics, including increased respiratory compliance, decreased elastance of the respiratory system, decreased respiratory tissue damping and elastance, and increased static respiratory tissue compliance. In some embodiments, the improvement in pulmonary mechanics of the subject with the chronic pulmonary disease can be at least about 5%, about 10%, about 15%, about 20%, about 25%, about 50%, or more.

In some embodiments, an agent that inhibits the renin-angiotensin signaling pathway can include an AGTR2 antagonist. AGTR2 antagonists can include any active compound that binds to the AGTR2 subtype and that suitably inhibits the effect of angiotensin II signaling through this receptor, including pharmaceutical compatible salts of the active compound. This category includes compounds having differing structural features. For example, in some embodiments, the AGTR2 antagonist is selected from 4,5,6,7-tetrahydro-1H-imidazo[4,5-c]pyridine-6-carboxylic acid analogs as described for example in U.S. Pat. No. 4,812,462 and especially in the compound claims of this patent. In illustrative examples of this type, the AGTR2 antagonist is selected from compounds having the formula (I):

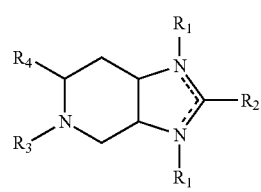

or their pharmaceutically compatible salts,
wherein — is a single or a double bond;
one of $R_1$ is present and is an alkyl of from four to twenty carbons, inclusive,

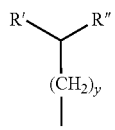

wherein y is zero, one, two, three, four or five, R' is cycloalkyl of from four to twenty carbons, inclusive in a one, two or three saturated ring system, said ring consisting of from four to eight carbons inclusive, each ring unsubstituted or substituted by a straight or branched lower alkyl group, naphthyl, heteroaryl consisting of 2-, 3-, or 4-pyridyl; 1-, 2-, or 4-imidazolyl; 1-, 2-, 3-, 4-, 5-, 6-, or 7-indolyl; 2-, or 3-thienyl; 2-, or 3-furyl; or 1-, 2-, or 3-pyrazolyl, phenyl unsubstituted or substituted with of from one through five substituents selected from the group consisting of lower alkyl, halo, trifluoromethyl, hydroxy, lower alkoxy, lower alkyl acyloxy, amino, N-lower monoalkylamino, N,N-lower dialkylamino, lower thioalkyl, lower alkylsulfonyl, nitro and NH(C=O)$R_{10}$, wherein $R_{10}$ is lower alkyl, phenyl unsubstituted or substituted by lower alkyl, or —NH$R_{11}$ wherein $R_{11}$ is hydrogen or lower alkyl, and R" is hydrogen, lower alkyl, cycloalkyl of from four to twenty carbons, inclusive in a one two or three saturated ring system, said ring consisting of from four to eight carbons inclusive, each ring unsubstituted or substituted by a straight or branched lower alkyl group, naphthyl, phenyl unsubstituted or substituted with of from one through five substituents selected from the group consisting of alkyl, halo, trifluoromethyl, amino, N-lower monoalkylamino, N,N-lower dialkylamino, lower thioalkyl, lower alkylsulfonyl, and nitro;

$R_2$ is hydrogen, halo, lower alkyl, R—(CH$_2$)—$_x$ wherein x is one, two, three, four, or five and R' is independently as defined above,

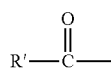

wherein R' is independently as defined above, or R'—CH(OH)— wherein R' is independently as defined above;

$R_3$ is R'—CH$_2$, wherein x and R' are independently as defined above,

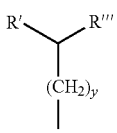

wherein R' and y are independently as defined above, and R''' is lower alkyl, cycloalkyl, of from four to twenty carbons, inclusive in a one, two or three saturated ring system, said ring consisting of from four to eight carbons inclusive, each ring unsubstituted or substituted by a straight or branched lower alkyl group, naphthyl, phenyl unsubstituted or substituted with of from one to five substituents selected from the group consisting of alkyl, halo, trifluoromethyl, amino, N-lower monoalkylamino, N,N-lower dialkylamino, lower thioalkyl, lower alkylsulfonyl, and nitro;

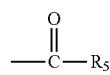

wherein $R_5$ is (i) alkyl of from one to fifteen carbons, inclusive, (ii)

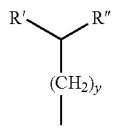

wherein R', R", and y are independently as defined above, CH=C$R_6R_1$ (iii) wherein $R_6$ is hydrogen or lower alkyl and $R_1$ is as defined above, (iv)

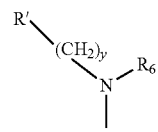

wherein y, R' and $R_6$ are independently as defined above, R'CH$_{2y}$—O— (v) wherein y and R' are independently as defined above, (vi)

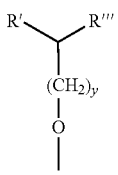

wherein R', R''', and y are independently as defined above, (d)

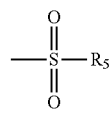

wherein $R_5$ is independently as defined above; (5) $R_4$ is (a) —CH$_2$ O$R_7$ wherein $R_7$ is hydrogen, lower acyl, a lower alkyl, (b)

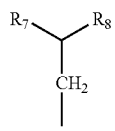

wherein $R_7$ is independently as defined above and $R_8$ is hydrogen, lower alkyl, or benzyl, (c)

—C≡N, (d)

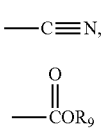
(e)

wherein $R_9$ is hydrogen, lower alkyl, or benzyl; and (6) n is one; with the overall proviso that $R_9$ cannot be hydrogen, methyl or ethyl when $R_3$ is R—$(CH_2)$—$_x$, or

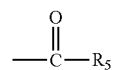

wherein $R_5$ is R'—$(CH_2)_y$O— or

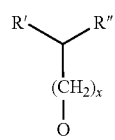

wherein each of R', R", x, and y are as defined above.

In some embodiments, the compounds according to formula (I) have a structure wherein $R_2$ is H, n is one and $R_3$ is

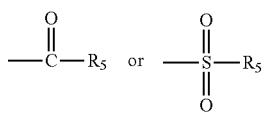

wherein $R_5$ is as defined above, $R_4$ is as defined above and $R_1$ is as defined above.

In some embodiments, the compounds according to formula (I) have a structure wherein $R_3$ is

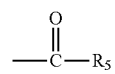

wherein $R_5$ is as defined above.

In specific embodiments, the compounds according to formula (I) are selected from: 1-(4-Dimethylamino-3-methylphenyl)methyl-5-diphenylacetyl-4,5,6,7-tetrahy-dro-1H-imidazo[4,5-c]-pyridine-6-carboxylic acid (PD-123,319); 1-(3-methyl-4-methoxyphenyl)-methyl-5-diphenylacetyl-4,5,6,7-tetrahydro-1-H-imidazo[4,5-c]pyridine-6-carboxylic acid (PD-121,981); and 1-(((4-amino-3-methylphenyl)methyl)-5-(diphenylacetyl)-4,5,6,7-tetrahydro-1H-imidazo(4,5c)pyridine-6-carboxylic acid (PD-123,177), or their prodrugs or pharmaceutically acceptable salts.

In other embodiments, the AGTR2 antagonist is selected from the compounds listed in U.S. Pat. No. 5,246,943. For example, the AGTR2 antagonist can include (S)-2-(Diphenylacetyl)-1,2,3,4-tetrahydro-6-methoxy-5-(phenylmethoxy)-3-isoquinolinecarboxylic acid, the synthesis of which is described in U.S. Pat. No. 5,246,943.

In still other embodiments, the AGTR2 antagonist is selected from the compounds listed in U.S. Pat. Nos. 5,348, 955, 5,441,959, 5,545,651, 5,789,415, and 8,551,950, all of which are incorporated by reference in their entirety.

In other embodiments, the AGTR2 antagonist is selected from antigen-binding molecules that are immuno-interactive with an AGTR2 polypeptide. Illustrative antigen-binding molecules include whole polyclonal antibodies. Such antibodies may be prepared, for example, by injecting an AGTR2 polypeptide or fragment thereof into a production species, which may include mice or rabbits, to obtain polyclonal antisera. Methods of producing polyclonal antibodies are well known to those skilled in the art. Exemplary protocols which may be used are described for example in Coligan et al., "Current Protocols In Immunology", (John Wiley & Sons, Inc, 1991), and Ausubel et al., (Current Protocols in Molecular Biology", John Wiley & Sons Inc, 1994-1998), in particular Section III of Chapter 11.

In lieu of the polyclonal antisera obtained in the production species, monoclonal antibodies may be produced using the standard method as described, for example, by Kohler and Milstein (1975, Nature 256, 495-497), or by more recent modifications thereof as described, for example, in Coligan et al., (1991, supra) by immortalizing spleen or other antibody-producing cells derived from a production species which has been inoculated with an AGTR2 polypeptide or fragment thereof.

The antigen-binding molecules can include Fv, Fab, Fab' and F(ab')$_2$ immunoglobulin fragments. Alternatively, the antigen-binding molecule may be in the form of a synthetic stabilized Fv fragment, a single variable region domain (also known as a dAbs), a "minibody" and the like as known in the art.

Also contemplated as antigen binding molecules are humanized antibodies. Humanized antibodies are produced by transferring complementary determining regions from heavy and light variable chains of a non human (e g, rodent, preferably mouse) immunoglobulin into a human variable domain. Typical residues of human antibodies are then substituted in the framework regions of the non human counterparts. The use of antibody components derived from humanized antibodies obviates potential problems associated with the immunogenicity of non human constant regions. General techniques for cloning non human, particularly murine, immunoglobulin variable domains are described, for example, by Orlandi et al. (1989, Proc. Natl. Acad. Sci. USA 86: 3833). Techniques for producing humanized monoclonal antibodies are described, for example, by Jones et al. (1986, Nature 321:522), Carter et al. (1992, Proc. Natl. Acad. Sci. USA 89: 4285), Sandhu (1992, Crit. Rev. Biotech. 12: 437), Singer et al. (1993, J. Immun 150: 2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997).

Illustrative antigen-binding molecules that are immuno-interactive with AGTR2 polypeptides and methods for their preparation are described by Nora et al. (1998, Am J Physiol. 275(4 Pt 2):H1395-403), Yiu et al. (1997, Regul Pept. 70(1):15-21), Reagan et al. (1993, Proc Natl Acad Sci USA. 90(17):7956-7960), Rakugi et al. (1997, Hypertens Res. 20(1):51-55) and Wang et al. (1998 Hypertension. 32(1):78-83), and some are available commercially, such as but not limited to H-143 (Santa Cruz Biotechnology, Santa Cruz, Calif.), which is directed against amino acid residues 221-363 from the carboxy terminus of human AT$_2$, rAT2 (Ab #1), which is directed against an 18-residue C-terminal fragment of rat $AT_2$), rAT2 (Ab #2) which is directed against an 18-residue C-terminal fragment of rat $AT_2$) and rAT2 (Ab #3), which is directed against a 10-residue N-terminal fragment of rat $AT_2$ (Alpha Diagnostic International, Inc.—5415 Lost Lane, SA).

In still other embodiments, the AGTR2 antagonist is selected from nucleic acid molecules that inhibit or otherwise reduce the level or functional activity of an expression product of an AGTR2 gene, illustrative examples of which include antisense molecules, ribozymes and RNAi molecules. Thus, the present invention contemplates antisense RNA and DNA molecules as well as ribozymes and RNAi molecules that function to inhibit the translation, for example, of AGTR2 mRNA. Antisense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an AGTR2 gene, are desirable. Exemplary antisense oligonucleotides can be derived from any nucleic acid molecule that encodes an AGTR2 receptor, such as those described in U.S. Pat. No. 5,556,780, and in U.S. Pat. Appl. Pub. No. 20030083339. Therapeutic methods utilizing antisense oligonucleotides have been described in the art, for example, in U.S. Pat. Nos. 5,627,158 and 5,734,033. Generally, antisense molecules comprise from about 8 to about 30 bases (i.e., from about 8 to about 30 linked nucleosides) and typically comprise from about 12 to about 25 bases.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of AGTR2 RNA sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to nucleic acid molecules may be introduced as a means of increasing intracellular stability and half-life. Possible modifications include but are not limited to the addition of flanking sequences of ribo- or deoxy-nucleotides to the 5' and/or 3' ends of the molecule or the use of artificial linkages rather than phosphodiesterase linkages within the oligodeoxyribonucleotide backbone. Illustrative modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or to 5'-2'. Various salts, mixed salts and free acid forms are also included.

Other agents that may be used to decrease the expression of an AGTR2 gene or the level and/or functional activity of an expression product of that gene include RNA molecules that mediate RNA interference (RNAi) of an AGTR2 gene or gene transcript. RNAi refers to interference with or destruction of the product of a target gene by introducing a single stranded, and typically a double stranded RNA (dsRNA), which is homologous to the transcript of the target gene. Thus, in one embodiment, dsRNA per se and especially dsRNA-producing constructs that encode an amino acid sequence corresponding to at least a portion of an AGTR2 polypeptide may be used to decrease its level and/or functional activity. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, Current Opinion in Genetics and Dev. 10: 562-567). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are preferably at least about 100 nucleotides in length. RNA-encoding constructs that express a single RNA designed to form a dsRNA via internal folding are preferably at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In another embodiment, RNA molecules of about 21 to about 23 nucleotides, which direct cleavage of specific mRNA to which they correspond, as for example described by Tuschl et al. in U.S. Patent Application Publication No. 20020086356, can be utilized for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5',3').

The AGTR2 antagonists described herein may be provided as salts with pharmaceutically compatible counterions. Pharmaceutically compatible salts refer to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically compatible salts are well known in the art. For example, S. M. Berge, et al. describe pharmaceutically compatible salts in detail in J. Pharmaceutical Sciences, 66: 1-19 (1977). The salts can be prepared in situ during the final isolation and purification of the active compounds of the invention, or separately by reacting the free base function with a suitable organic acid. Examples of pharmaceutically compatible, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically compatible salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically compatible salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

Pharmaceutical compositions include compositions wherein the pharmaceutically active compounds (e.g., AGTR2 antagonists) are contained in an effective amount to achieve their intended purpose. The dose of active compounds administered to a patient should be sufficient to achieve a beneficial response in the patient over time such as a reduction in at least one symptom associated with the pulmonary disease. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In any event, those of skill in the art may readily determine suitable dosages of the AGTR2 antagonists of the invention.

An effective amount of an AGTR2 antagonist is one that is effective for treating or preventing the symptoms associated with the pulmonary disease, including the prevention of incurring a symptom, holding in check such symptoms, and/or treating existing symptoms associated with the pulmonary disease. Modes of administration, amounts of AGTR2 antagonist administered, and AGTR2 antagonist formulations, for use in the methods described herein. Whether the pulmonary disease has been treated is determined by measuring one or more diagnostic parameters indicative of the course of the disease, compared to a suitable control. In the case of an animal experiment, a "suitable control" is an animal not treated with the AGTR2 antagonist, or treated with the pharmaceutical composition without the AGTR2 antagonist. In the case of a human subject, a "suitable control" may be the individual before treatment, or may be a human (e.g., an age-matched or similar control) treated with a placebo.

Therapeutically effective dosage amounts of AGTR2 antagonist, including derivatives and analogs may be present in varying amounts in various embodiments. For example, in some embodiments, a therapeutically effective amount of an AGTR2 antagonist may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, an AGTR2 antagonist is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, AGTR2 antagonist is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount may be, for example, about 0.0001 mg/kg weight to 0.1 mg/kg weight, e.g., from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage may be a dosage of 10 µg/kg/day, 50 µg/day, 75 µg/kg/day, 100 µg/kg/day, 250 µg/kg/day, 500 µg/kg/day, 1000 µg/kg/day or more. In various embodiments, the amount of AGTR2 antagonist or pharmaceutical salt thereof is sufficient to provide a dosage to a patient of between 0.01 µg/kg and 10 mg/kg; 0.1 µg/kg and 5 mg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

In some embodiments, the AGTR2 antagonist can be administered to the subject in need thereof in combination with at least one of an angiotensin-converting enzyme (ACE) inhibitor, renin inhibitor, or angiotensin II receptor type I (AGTR1) agonist.

The mechanism of action for ACE inhibitors is via an inhibition of angiotensin-converting enzyme (ACE) that prevents conversion of angiotensin I to angiotensin II, a potent vasoconstrictor, resulting in lower levels of angiotensin II, which causes a consequent increase in plasma renin activity and a reduction in aldosterone secretion. The term ACE inhibitor is intended to embrace any agent or compound, or a combination of two or more agents or compounds, having the ability to block, partially or completely, the rapid enzymatic conversion of the physiologically inactive decapeptide form of angiotensin ("Angiotensin I") to the vasoconstrictive octapeptide form of angiotensin ("Angiotensin II").

Examples of ACE inhibitors include, without limitation, the following compounds: AB-103, ancovenin, benazeprilat, BRL-36378, BW-A575C, CGS-13928C, CL242817, CV-5975, Equaten, EU4865, EU-4867, EU-5476, foroxymithine, FPL 66564, FR-900456, Hoe-065, 15B2, indolapril, ketomethylureas, KRI-1177, KR1-1230, L681176, libenzapril, MCD, MDL-27088, MDL-27467A, moveltipril, MS41, nicotianamine, pentopril, phenacein, pivopril, rentiapril, RG-5975, RG-6134, RG-6207, RGH0399, ROO-911, RS-10085-197, RS-2039, RS 5139, RS 86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y-23785, Yissum, P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, I (-(I-carboxy-6-(4-piperidinyl)hexyl)amino)-1-oxo-propyl octahydro-1H-indole-2-carboxylic acid, Bioproject BP1137, Chiesi CHF 1514, Fisons FPL-66564, idrapril, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, tranolapril, trandolaprilat, ceranapril, moexipril, quinaprilat spirapril, and combinations thereof.

The phrase "ACE inhibitor" also embraces so-called NEP/ACE inhibitors (also referred to as selective or dual acting neutral endopeptidase inhibitors) which possess neutral endopeptidase (NEP) inhibitory activity and angiotensin converting enzyme (ACE) inhibitory activity. Examples of NEP/ACE inhibitors particularly preferred and suitable for use herein are those disclosed in U.S. Pat. Nos. 5,508,272, 5,362,727, 5,366,973, 5,430,145, 5,225,401, 4,722,810, 5,223,516, 5,508,272, 5,552,397, 4,749,688, 5,504,080, 5,612,359, 5,525,723, 5,430,145, and 5,679,671, and European Patent Applications 0481522, 0534263, 0534396, 0534492, and 0671172, each of which is hereby incorporated by reference in its entirety.

Examples of AGTR1 agonists can include angiotensin peptide analog [Val5]-angiontensin II acetate salt and non-peptide L-162,313, which are commercially available form Sigma-Aldrich.

Examples of a renin inhibitor include pepstatin, CGP2928, remikiren, enalkiren, zenkiren, and aliskiren.

Various embodiments may include differing dosing regimen. In some embodiments, the AGTR2 antagonist is administered via continuous infusion. In some embodiments, the continuous infusion is intravenous. In other embodiments, the continuous infusion is subcutaneous. Alternatively or additionally, in some embodiments, the AGTR2 antagonist is administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

The AGTR2 antagonist may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, inhaled, intranasal, or intraocular injections. For injection, the therapeutic agents of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Alternatively, the compositions can be formulated for local or topical administration. In this instance, the subject compositions may be formulated in any suitable manner, including, but not limited to, creams, gels, oils, ointments, solutions and suppositories. Such topical compositions may include a penetration enhancer such as benzalkonium chloride, digitonin, dihydrocytochalasin B, capric acid, increasing pH from 7.0 to 8.0. Penetration enhancers which are directed to enhancing penetration of the active compounds through the epidermis are preferred in this regard. Alternatively, the topical compositions may include liposomes in which the active compounds of the invention are encapsulated.

The compositions may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the active compounds invention can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceuticals which can be used orally include push-fit capsules made of gelatine, as well as soft, sealed capsules made of gelatine and a plasticiser, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the active compounds may also include injecting or implanting controlled releasing devices designed specifically for this purpose or other forms of implants modified to act additionally in this fashion. Controlled release of an active compound of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres.

The active compounds may be administered over a period of hours, days, weeks, or months, depending on several factors, including the severity of the inflammatory pain being treated, whether a recurrence of the inflammatory pain is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The compositions may also be administered to the respiratory tract as a nasal or pulmonary inhalation aerosol or solution for a nebuliser, or as a microtine powder for insufflation, alone or in combination with an inert carrier such as lactose, or with other pharmaceutically acceptable excipients. In such a case, the particles of the formulation may advantageously have diameters of less than 50 micrometers, suitably less than 10 micrometers.

Example 1

We conducted a genome wide association study (GWAS) to identify potential genetic sources of clinical variation in CF pulmonary symptoms, in hopes of identifying new therapeutic targets. The CF Gene Modifier Consortium was comprised of three independently generated cohorts of subjects with CF (6,365 total CF patients), and examined over 8 million genetic variants to determine which areas of the genome associate with differences in forced expiratory volume in one second ($FEV_1$), which is a marker of pulmonary disease severity. A region on the X chromosome, containing the type 2 angiotensin II receptor gene, AGTR2, reached the highest significance ($p=1.25\times10^{-7}$) when all subjects were combined. In clinical terms, our model predicted an average decrease in $FEV_1$ at age 20 years of 11% in females and 5.6% in males for those with the adverse AGTR2 genotype. (Table 1).

TABLE 1

| Percent Predicted FEV1 (patient specific estimates, age 20) for CF patients | | | |
|---|---|---|---|
| Genotype rs1403543 | Total (n) | Female (n) | Male (n) |
| GG | 72.36% (540) | 73.89% (126) | 71.76% (338) |
| GA | 65.98% (303) | 65.98% (298) | NA |
| AA | 65.03% (401) | 62.73% (157) | 66.10% (326) |

The Role of AGTR2 in Lung Disease

In contrast to AGTR1, much less is known about angiotensin II signaling through the AGTR2 receptor. Signaling through AGTR2 has been shown to have both adverse and beneficial effects on inflammation and fibrosis. While Agtr2 deficient mice have significantly worse cardiac function following acute myocardial infarction, decreased signaling through the AGTR2 receptor may be beneficial in lung disease. For example, blocking Agtr2 signaling attenuates lung fibrosis and decreases migration and proliferation of fibrotic fibroblasts in bleomycin-induced lung fibrosis in mice. Further, hypoxia-induced collagen synthesis of human lung fibroblasts is attenuated by the inhibition of AGTR2. The downstream effects of ligand binding to AGTR2 are incompletely understood. There is evidence of increased nitric oxide synthesis following angiotensin binding to AGTR2, and the receptor appears to be involved in apoptosis. Additional studies have shown that AGTR2 inhibits proliferation in coronary endothelial cells and stimulates angiogenesis in an alginate implant model. Initial expression studies indicated AGTR2 was highly expressed in fetal tissues but found only in the brain and adrenal glands of adults and therefore was not likely to play a role in blood-pressure regulation in adults. More recently, AGTR2 expression has been localized in additional adult tissues, including lung, where is it found in bronchi and airway epithelial cells, mucous glands, vascular endothelial cells, fibroblasts, chondrocytes, and macrophages. Furthermore, AGTR2 expression by lung fibroblasts is increased in experimental lung fibrosis CF Mouse Pulmonary Phenotype We have previously found that F508del CF mice exhibit an increased respiratory rate, and heightened immune response to infection. We recently used a forced mechanical oscillation procedure to evaluate pulmonary mechanics in CF mice (DF508 congenic C57bl/6). We determined that CF mice have decreased compliance and increased elastance of their overall respiratory system, along with altered airway tissue elastance, damping, and static compliance (FIG. 1). Finally the overall shape of the inhalation/exhalation curve (known as the shape parameter) in CF mice is also significantly altered. Taken together, these findings indicate increased impedance of the small airways in CF mice, as differences in CF mouse pulmonary mechanics were confined to the peripheral tissues, which include the distal airways and lung parenchyma itself. This is consistent with the pulmonary phenotype of CF patients, where significant increases in small airways resistance may occur even in patients with normal spirometry.

Figure 2:
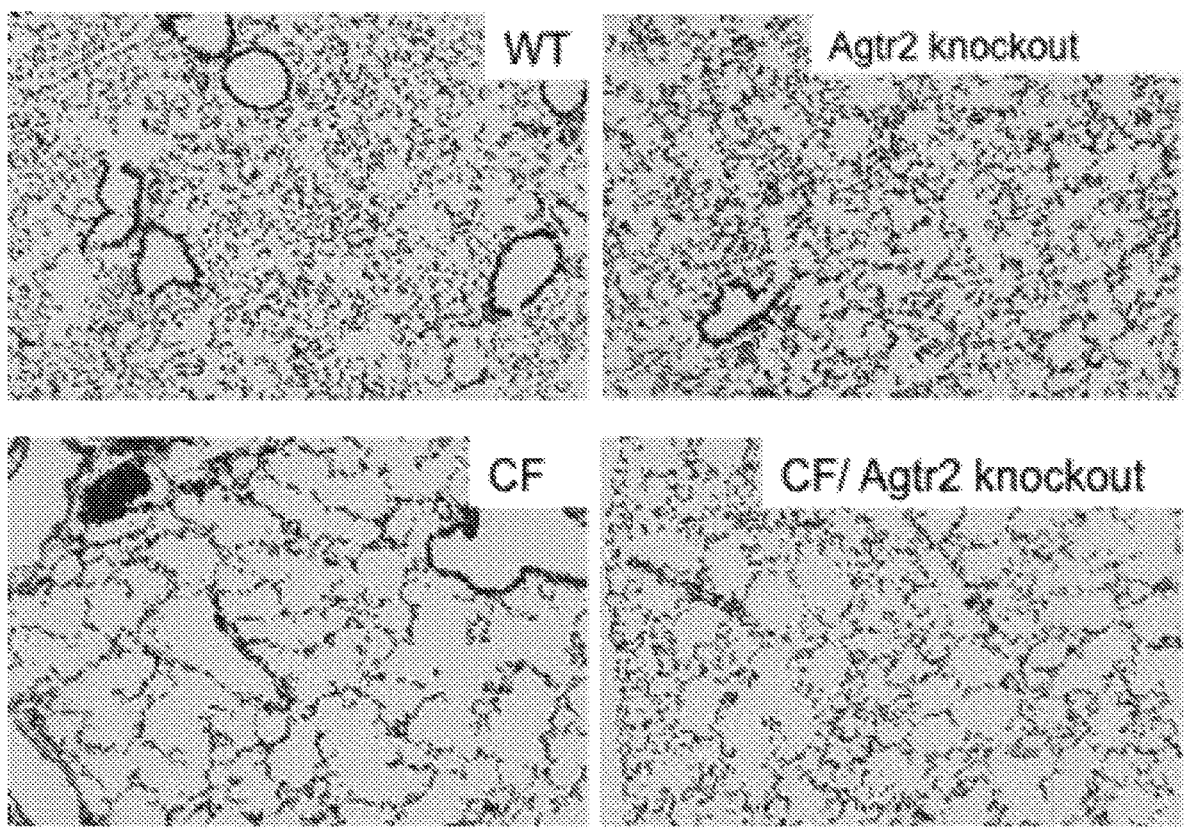
FIG. 2 illustrates images showing CF mice display distal airway enlargement (lower left panel) compared to wild type (WT) mice (upper left panel). The Agtr2 knockout mouse (upper right panel) is indistinguishable from WT, but the double knockout (CF/Agtr2 knockout; lower right panel) shows some evidence of correction of this phenotype.
Figure 3:
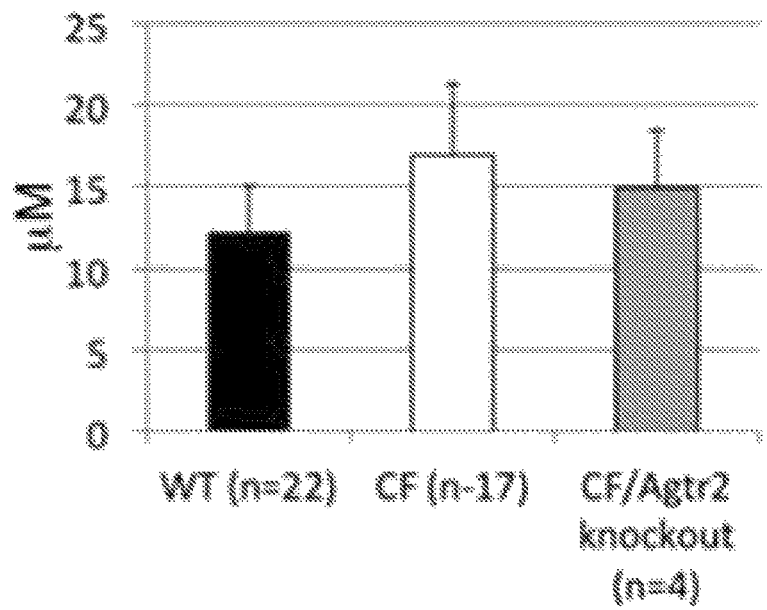
FIG. 3 is a graph showing quantification of distal airway enlargement using a mean linear intercept calculation.

The development of small airways disease in CF mice would be expected to result in distal airway enlargement and gas trapping. To further evaluate this possibility, lung histology of CF mice was compared to wild-type controls (FIG. 2). CF mice exhibited increased mean linear intercept distances suggestive of distal airway enlargement and gas trapping (FIG. 2). Taken together, these data identify that CF mice exhibit histologic evidence of gas trapping without destructive emphysema, which recapitulates features of early CF lung disease in humans.

Loss of Agtr2 in the CF Mouse Prevents the CF-Specific Pulmonary Phenotype Described Above Since the GWAS data indicated that genetic variation near the AGTR2 genetic locus alters CF pulmonary phenotype, we decided to determine whether the described CF pulmonary phenotype would be altered by genetic loss of AGTR2 in a CF mouse model. The gene for AGTR2 is on the X chromosome in both mice and humans and is noted as AGTR2 in humans and Agtr2 in mice. The gene consists of only 3 exons, with exon 3 containing the entire coding sequence. We have acquired mice carrying null (knockout) alleles of Agtr2. Previous studies have identified changes in blood-pressure regulation and cognitive function in these mice, but pulmonary function in the absence of Agtr2 has not been previously assessed. We have crossed Agtr2 knockout mice with CF mice, to create mice homozygous for both CF and Agtr2 knockout. We used the same forced oscillation technique previously published to characterize the pulmonary mechanics of the double knockout mice (CF/Agtr2 knockout), as well as the Agtr2 knockout alone. Our results (presented here for the first time) indicate that while the Agtr2 knockout mouse alone does not have a pulmonary phenotype that differs from WT mice, the loss of Agtr2 in the CF mouse reverses the observable CF pulmonary phenotype to close to WT levels (FIG. 1 and FIG. 2). Specifically, the respiratory system compliance and elastance were restored to near normal levels in the double knockout mice, as were the tissue elastance, tissue damping, and static tissue compliance. The only pulmonary measurement that was not improved by loss of Agtr2 in the CF mouse was the shape parameter, which refers to the overall inhalation/exhalation curve and therefore breathing pattern (FIG. 1). Therefore, genetic loss of Agtr2 in CF mice prevents the development of most aspects of CF-related pulmonary disease measured here.

Treatment of CF Mice with an Agtr2 Blocker Improves CF-Related Pulmonary Disease Constitutive genetic loss of Agtr2 prevents the development of CF-related pulmonary disease, but it was unknown whether these results would be achievable pharmacologically. Drugs exist that are designed to specifically block the AGTR2 receptor, and we used one of these drugs to determine whether the same benefits may be achievable through pharmaceutical intervention. Briefly, CF mice were treated via subcutaneous injection of EMA200 (PD123319), available from Sigma Pharmaceuticals), at a dose of 2 mg/kg per day. The mice were treated from age 3 weeks through adulthood (16 weeks), 5 days per week. At 16 weeks, the pulmonary mechanics of the mice were assessed using the forced oscillation technique (FIG. 1). Lung tissue was obtained following the forced oscillation measurements, and will be used to determine whether drug treatment improved the distal airway enlargement indicative of CF.

The results from these experiments showed that treatment with the AGTR2 blocker EMA200 successfully restored/prevented all aspects of pulmonary disease in CF mice, with the exception again of the shape parameter (that was also not improved by genetic loss of Agtr2) (FIG. 1). These results demonstrate that loss of Agtr2 is beneficial for the prevention/treatment of CF-specific lung disease, and are achievable through pharmacologic blocking of the AGTR2 receptor with EMA200.

Interestingly, there were 2 groups of CF mice used in the drug study—one control group received daily injections of saline, while the other group of CF mice received daily injections of the EMA200 drug. Of the CF mice that received the saline, 5/6 mice died during the course of the study (thus we do not have pulmonary function data for this group). The 6 CF mice that received daily injections of the EMA200 all survived, and appeared much healthier than control untreated CF mice (who typically have a 50% survival rate). Therefore, in addition to improving pulmonary function, daily treatment with EMA200 dramatically improved survival of the CF mice.

Relevance to Asthma and COPD

There is reason to believe that targeting the renin-angiotensin signaling pathway may be beneficial for other lung diseases, specifically asthma and chronic obstructive pulmonary disease (COPD). First, cystic fibrosis shares many pathologic similarities with these two diseases, in terms of alterations to the pulmonary mechanics including changes in respiratory system elastance, compliance, tissue damping, and distal airway structure. The fact that loss of Agtr2, and further inhibition with an Agtr2 blocker attenuates these phenotypes in CF mice leads us to believe they will also improve these same phenotypes in asthma and/or COPD. Second, the expression of both angiotensin II receptors (AGTR1 and AGTR2) is increased in the lungs of human adults with COPD. The amount of AGTR1 was increased tenfold and that of AGTR2 fivefold in individuals with COPD compared to the levels in control lungs (both normal and non-COPD smokers). Finally a meta-analysis of asthma susceptibility genes in the Chinese population identified an insertion/deletion polymorphism in angiotensin converting enzyme (ACE) as one of seven genetic variants significantly associated with the risk of asthma. Therefore, we suspect that reducing signaling through AGTR2 in COPD and asthma will have beneficial effects.

Clinical Data Related to ACE Inhibitors and ARBs in CF Patients

There are CF patients who are prescribed ACE inhibitors or ABRs for hypertension unrelated to CF. We have obtained preliminary data from the Cystic Fibrosis Clinic at Rainbow Babies and Children's Hospital that indicates that approximately 10% of the CF patients have been diagnosed with hypertension. Many of these patients have been prescribed either an ACE inhibitor or an angiotensin receptor blocker (ARB). We used a chart review to compare the pulmonary function (in $FEV_1$ percent predicted for age, gender, and size) of those CF patients taking either an ACE inhibitor (blocks upstream of both AGTR1 and AGTR2) or an ARB (specifically blocks AGTR1, thus potentially increasing binding through AGTR2) to age matched CF patients not taking either drug. The patients currently taking the ACE inhibitors have an average $FEV_1$ that is approximately 7% higher than age matched controls (68% pulmonary function vs. 61% pulmonary function), while those taking an ARB had approximately 8% lower pulmonary function (55% pulmonary function vs. 63% pulmonary function). Taken together, these data indicate that the pulmonary function of those CF patients taking an ACE inhibitor was approximately 13% higher than those taking an ARB. This is consistent with what we would have predicted given the pathway.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

What is claimed is:

1. A method of treating a subject who has or is at risk of cystic fibrosis, or chronic obstructive pulmonary disease, the method comprising:
administering to the subject a therapeutically effective amount of an AGTR2 antagonist.

2. The method of claim 1, wherein the AGTR2 antagonist comprises 4,5,6,7-tetrahydro-1H-imidazo[4,5-c]pyridine-6-carboxylic acid analog.

3. The method of claim 1, wherein the AGTR2 antagonist is selected from the group consisting of 1-(4-Dimethylamino-3-methylphenyl)methyl-5-diphenylacetyl-4,5,6,7-tetrahy-dro-1H-imidazo[4,5-c]-pyridine-6-carboxylic acid (PD-123,319); 1-(3-methyl-4-methoxyphenyl)-methyl-5-diphenylacetyl-4,5,6,7-tetrahydro-1-H-imidazo[4,5-c]pyridine-6-carboxylic acid (PD-121,981); and 1-((4-amino-3-methylphenyl)methyl)-5-(diphenylacetyl)-4,5,6,7-tetrahydro-1H-imidazo(4,5c)pyridine-6-carboxylic acid (PD-123,177), (S)-2-(Diphenylacetyl)-1,2,3,4-tetrahydro-6-methoxy-5-(phenylmethoxy)-3-isoquinolinecarboxylic acid, and pharmaceutically acceptable salts thereof.

4. The method of claim 1, wherein the AGTR2 antagonist is administered at amount effective to provide improvements to pulmonary function and/or lung mechanics and/or airway resistance.

5. The method of claim 4, wherein the improvements to pulmonary function and/or lung mechanics and/or airway resistance include at least one of increased respiratory compliance, decreased elastance of the respiratory system, decreased respiratory tissue damping and elastance, or increased static respiratory tissue compliance.

6. The method of claim 1, further comprising administering to the subject a therapeutically effective amount of at least one of an ACE inhibitor or a renin inhibitor.

7. A method of treating cystic fibrosis or chronic obstructive pulmonary disease in a subject, the method comprising:
administering to the subject a therapeutically effective amount of an AGTR2 antagonist, wherein the AGTR2 antagonist comprises a 4,5,6,7-tetrahydro-1H-imidazo[4,5-c]pyridine-6-carboxylic acid analog.

8. The method of claim 7, wherein the AGTR2 antagonist is selected from the group consisting of 1-(4-Dimethyl-amino-3-methylphenyl)methyl-5-diphenylacetyl-4,5,6,7-tetrahy-dro-1H-imidazo[4,5-c]-pyridine-6-carboxylic acid (PD-123,319); 1-(3-methyl-4-methoxyphenyl)-methyl-5-diphenylacetyl-4,5,6,7-tetrahydro-1-H-imidazo[4,5-c]pyridine-6-carboxylic acid (PD-121,981); and 1-((4-amino-3-methylphenyl)methyl)-5-(diphenylacetyl)-4,5,6,7-tetrahydro-1H-imidazo(4,5c)pyridine-6-carboxylic acid (PD-123,177), (S)-2-(Diphenylacetyl)-1,2,3,4-tetrahydro-6-methoxy-5-(phenylmethoxy)-3-isoquinolinecarboxylic acid, their prodrugs, and pharmaceutically acceptable salts thereof.

9. The method of claim 7, wherein the AGTR2 antagonist is 1-(4-Dimethylamino-3-methylphenyl)methyl-5-diphenylacetyl-4,5,6,7-tetrahy-dro-1H-imidazo[4,5-c]-pyridine-6-carboxylic acid (PD-123,319) and pharmaceutically acceptable salts thereof.

10. A method of treating cystic fibrosis or chronic obstructive pulmonary disease in a subject, the method comprising:
administering to the subject a therapeutically effective amount of an AGTR2 antagonist, wherein the AGTR2 antagonist is 1-(4-Dimethylamino-3-methylphenyl)methyl-5-diphenylacetyl-4,5,6,7-tetrahy-dro-1H-imidazo[4,5-c]-pyridine-6-carboxylic acid (PD-123,319) or a pharmaceutically acceptable salt thereof.

* * * * *